Figure 1:
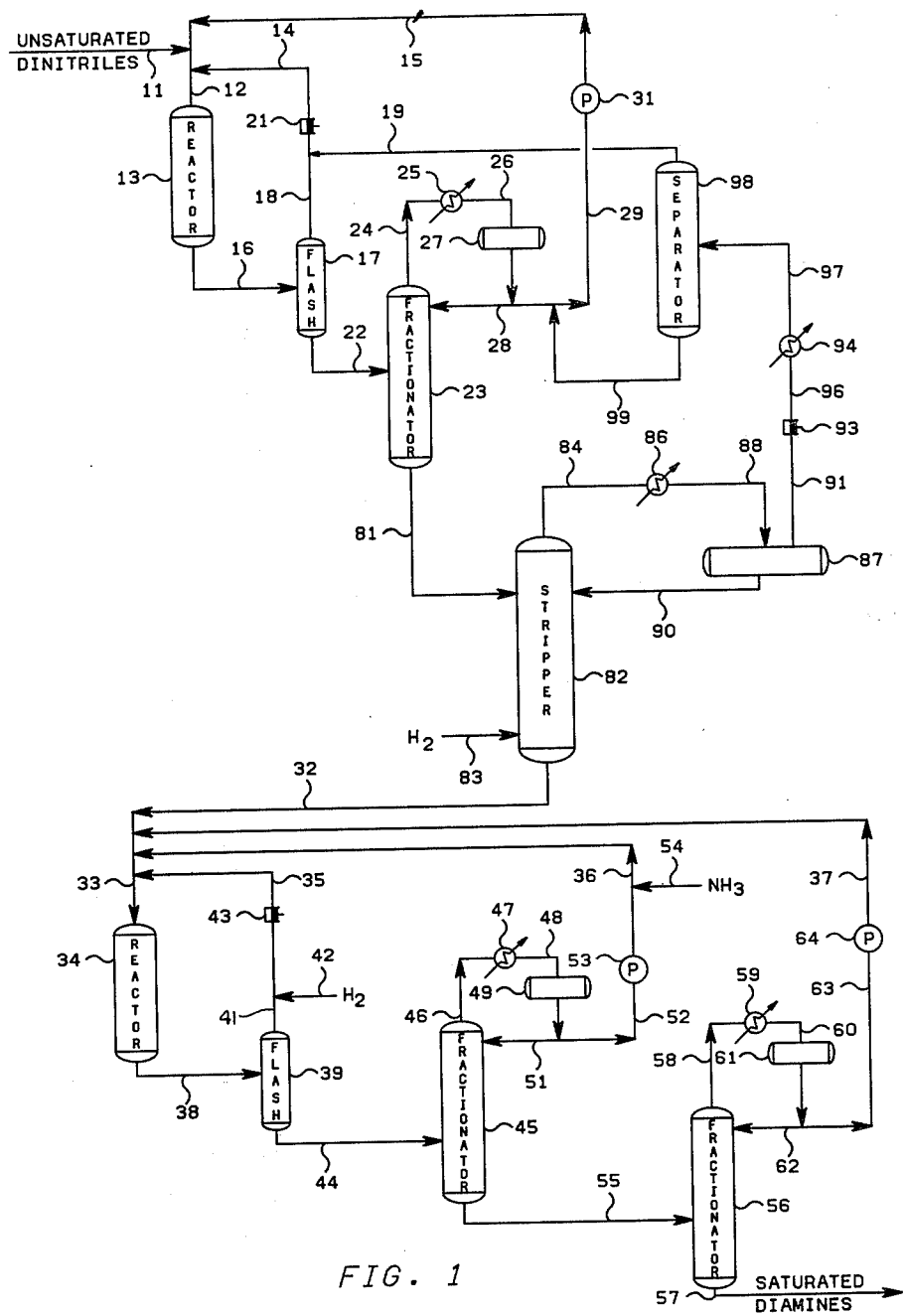

United States Patent [19]

Irvin

[11] 4,320,091
[45] Mar. 16, 1982

[54] APPARATUS FOR TWO STAGE CATALYTIC HYDROGENATION OF OLEFINICALLY UNSATURATED DINITRILES

[75] Inventor: Howard B. Irvin, Bartlesville, Okla.

[73] Assignee: Phillips Petroleum Company, Bartlesville, Okla.

[21] Appl. No.: 210,503

[22] Filed: Nov. 26, 1980

Related U.S. Application Data

[62] Division of Ser. No. 74,708, Sep. 12, 1979, Pat. No. 4,263,228.

[51] Int. Cl.³ .......................... B01J 8/02; B01J 19/24
[52] U.S. Cl. .................................. 422/190; 422/211
[58] Field of Search ...................... 422/189, 190, 211

[56] References Cited

U.S. PATENT DOCUMENTS

| | | | |
|---|---|---|---|
| 3,193,488 | 7/1965 | Carr | 422/189 |
| 3,389,075 | 6/1968 | Addison | 422/189 |
| 3,563,976 | 2/1971 | Mills | 564/491 |
| 3,804,918 | 4/1974 | Henderson | 422/189 |
| 3,880,929 | 4/1975 | Drake | 564/491 |
| 3,896,173 | 7/1975 | Drake | 564/491 |
| 4,003,933 | 1/1977 | Drake | 564/491 |

*Primary Examiner*—Bradley Garris

[57] ABSTRACT

An olefinically unsaturated dinitrile of the formula

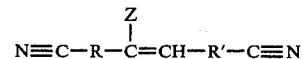

wherein R and R' are alkylene or alkylidene radicals and Z is an alkyl radical which is converted to the corresponding saturated dinitrile in the presence of hydrogen, a palladium catalyst and at least one alkanol having 1 to 3 carbon atoms. The saturated dinitrile is then converted to the corresponding diamine in the presence of hydrogen, a secondary amine formation suppressant, a ruthenium catalyst and at least one diluent selected from the group consisting of tertiary alkanols having 4 to 12 carbon atoms, saturated hydrocarbons having 4 to 12 carbon atoms, and ethers having 4 to 12 carbon atoms. The at least one alkanol is substantially completely separated from the saturated dinitrile before the saturated dinitrile is converted to the corresponding diamine to avoid N-alkylation reactions which may occur if the at least one alkanol is present when the saturated dinitrile is converted to the corresponding diamine.

7 Claims, 1 Drawing Figure

APPARATUS FOR TWO STAGE CATALYTIC HYDROGENATION OF OLEFINICALLY UNSATURATED DINITRILES

This application is a division of application Ser. No. 074,708, filed Sept. 12, 1979, now U.S. Pat. No. 4,263,228.

This invention relates to a two-step process for the preparation of unsaturated aliphatic diamines by the catalytic hydrogenation of olefinically unsaturated aliphatic dinitriles. In another aspect this invention relates to method and apparatus for substantially removing the diluent utilized in the first stage of the two-step process before the reaction effluent from the first stage of the two-step process is introduced into the second stage of the two-step process. In another aspect this invention relates to method and apparatus for improving the energy efficiency of a two-step process for the preparation of unsaturated aliphatic diamines by the catalytic hydrogenation of olefinically unsaturated aliphatic dinitriles.

A two-step process is known in the prior art for the preparation of saturated aliphatic diamines by the catalytic hydrogenation of olefinically unsaturated aliphatic dinitriles. An olefinically unsaturated dinitrile of the formula

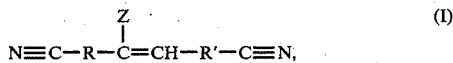

$$N\equiv C-R-\underset{|}{\overset{Z}{C}}=CH-R'-C\equiv N, \quad (I)$$

wherein R and R' are alkylene or alkylidene radicals and Z is an alkyl radical, is converted to the corresponding saturated dinitrile in the presence of hydrogen, a palladium catalyst and at least one alkanol having 1 to 3 carbon atoms. The saturated dinitrile is then converted to the corresponding diamine in the presence of hydrogen, a secondary diamine formation suppressant, a ruthenium catalyst and at least one diluent selected from the group consisting of tertiary alkanols having 4 to 12 carbon atoms, saturated hydrocarbons having 4 to 12 carbon atoms, and ethers having 4 to 12 carbon atoms. The prior art further discloses that the presence of the first diluent which is present in the first step of the two-step process, is undesirable in the second step of the two-step process because the presence of the at least one alkanol causes n-alkylation reactions if present when the saturated dinitrile is converted to the corresponding diamine. It has been suggested that a fractionator be utilized to remove the at least one alkanol from the saturated dinitrile before the saturated dinitrile is converted to the corresponding diamine. However, it has been determined that the concentration of the at least one alkanol in the reaction effluent containing the saturated dinitrile is undesirably high even when the fractionator is used to separate the at least one alkanol from the saturated dinitrile. It has further been determined that the energy required when using a fractionator to substantially remove the at least one alkanol from the reaction effluent containing the saturated dinitrile would be unacceptable in a commercial operation.

It is thus an object of this invention to provide method and apparatus for substantially removing the diluent utilized in the first stage of a two-step process before the reaction effluent from the first stage of the two-step process is introduced into the second stage of the two-step process. It is another object of this invention to provide method and apparatus for improving the energy efficiency of a two-step process for the preparation of saturated aliphatic diamines by the catalytic hydrogenation of olefinically unsaturated aliphatic dinitriles.

In accordance with the present invention, method and apparatus is provided whereby olefinically unsaturated dinitriles of formula (I) are converted to the corresponding saturated dinitriles in the presence of hydrogen, a palladium catalyst and at least one alkanol having 1 to 3 carbon atoms. The hydrogen in the reaction effluent flowing from the first reactor is removed in a flash tank, compressed and recirculated to the first reactor. The principal portion of the at least one alkanol in the reaction effluent flowing from the first reactor is separated from the saturated dinitrile in a fractionator. The separated at least one alkanol is recycled to the first reactor. The bottoms product from the fractionator will consist essentially of the saturated dinitrile with only a small concentration of the at least one alkanol. However, even though the concentration of the at least one alkanol is low, the concentration will still be higher than desirable for the second stage of the two-stage process. The bottoms product from the fractionator is thus provided to a stripping column and hydrogen is utilized to substantially strip the at least one alkanol from the saturated dinitriles. The stripped at least one alkanol is recycled to the first reactor as is the hydrogen which is utilized to strip that at least one alkanol. The bottoms product from the stripper is then provided to the second stage of the two-stage process and the saturated dinitriles are converted to the corresponding diamine in the presence of hydrogen, a secondary amine formation suppressant, a ruthenium catalyst and at least one diluent selected from the group consisting of tertiary alkanols having 4 to 12 carbon atoms, saturated hydrocarbons having 4 to 12 carbon atoms, and ethers having 4 to 12 carbon atoms.

Other objects and advantages of the invention will be apparent from the foregoing brief description of the invention and from the claims as well as from the detailed description of the drawing which is a diagrammatic illustration of the two-step process for the preparation of saturated aliphatic diamines by the catalytic hydrogenation of olefinically unsaturated aliphatic dinitriles.

Referring now to the drawing, a feedstream comprising branched-chain unsaturated aliphatic dinitriles is passed through conduits 11 and 12 into tickle bed reactor 13 along with hydrogen from conduit 14 and a first diluent, which is preferably methanol, from conduit 15. The reactor 13 is operated under reaction conditions suitable to at least substantially reduce the olefinic unsaturation without any significant reduction of the nitrile groups. The reaction effluent, comprising saturated dinitriles, first diluent and hydrogen, is passed through conduit 16 into a flash tank 17 for the recovery of the unreacted hydrogen. The hydrogen is withdrawn from flash tank 17 by way of conduit 18, combined with hydrogen from conduit 19, compressed by compressor 21 and passed through conduits 14 and 12 to reactor 13. The liquid is withdrawn from flash tank 17 and passed by way of conduit 22 into an intermediate portion of fractionator 23 for the removal of the diluent. The vaporous first diluent is withdrawn from an upper portion of fractionator 23 by way of conduit 24, condensed in heat exchanger 25 and passed by way of conduit 26 into accumulator 27. A portion of the liquid from accumulator 27 can be passed through conduit 28 to an upper portion of fractionator 23 as reflux, while the remaining liquid is passed through conduit 29, pump 31 and conduits 15 and 12 to reactor 13.

The liquid dinitriles, which still contain a small concentration of the first diluent, are withdrawn from a lower portion of fractionator 23 and passed through conduit means 81 to the stripping column 82. Hydrogen is passed to a lower portion of the stripping column 82 through conduit means 83. Since the first diluent will be the most volatile component of the effluent flowing through conduit means 81, the first diluent will be essentially stripped from the dinitriles by the hydrogen flowing through the stripping column 82. The thus stripped first diluent and the hydrogen will be passed as an overhead stream from the stripping column 82 through conduit means 84. The overhead stream flowing through conduit means 84 will be at least partially condensed in heat exchanger 86 and will be provided to the overhead accumulator 87 through conduit means 88. The hydrogen and the principal portion of the first diluent will remain in gaseous form and will be provided from the overhead accumulator 87 through conduit means 91 to the compressor 93. The hydrogen and the principal portion of the first diluent will be provided from the compressor 93 through conduit means 96 to the heat exchange cooler 94. The hydrogen and the at least partially condensed first diluent will be provided from the heat exchanger 94 through conduit 97 to to the separator 98. The first diluent is provided as a bottoms from the separator 98 through conduit 99 to conduit 29 and is thus recycled to the reactor 13. The hydrogen is provided as an overhead from the separator 98 through conduit 19 and is thus recycled to the reactor 13.

The condensate from the overhead accumulator 87 will be returned through conduit 90 to the stripping column 82 as external reflux therefor. The liquid dinitriles, from which the first diluent utilized in reactor 13 has been substantially removed, are withdrawn from a lower portion of the stripping column 82 and passed through conduits 32 and 33 into the second stage reactor 34 along with hydrogen from conduit means 35, ammonia from conduit means 36, and a second diluent, which is preferably at least one tertiary alkanol, from conduit means 37.

The reactor 34 is operated under reaction conditions suitable to convert at least substantially the nitrile groups to primary amine groups and to reduce any olefinic unsaturation in the feed to reactor 34. The effluent from reactor 34 is passed through conduit 38 to a flash tank 39 for the recovery of the unreacted hydrogen. The hydrogen is withdrawn from flash tank 39 by way of conduit 41, combined with make-up hydrogen from conduit 42, compressed by compressor 43 and passed through conduits 35 and 33 to reactor 34. The liquid is withdrawn from flash tank 39 and passed by way of conduit 44 into an intermediate portion of fractionator 45 for removal of ammonia. The vaporous ammonia is withdrawn from an upper portion of fractionator 45 by way of conduit 46, condensed in heat exchanger 47, and passed by way of conduit 48 into accumulator 49. A portion of the liquid from accumulator 49 can be passed through conduit 51 to an upper portion of fractionator 45 as reflux, while the remainder of the liquid from accumulator 49 is passed by way of conduit 52, pump 53 and conduit 36, along with make-up ammonia from conduit 54, into second reactor 34. The liquid effluent from the lower portion of fractionator 45, which comprises the second diluent and saturated diamine products, is passed through conduit 55 into an intermediate portion of fractionator 56. A bottoms stream comprising saturated diamines is withdrawn from a lower portion of fractionator 56 by way of conduit 57. A vaporous overhead stream comprising the second diluent is withdrawn from an upper portion of fractionator 56 by way of conduit 58, condensed in heat exchanger 59, and passed by way of conduit 60 into accumulator 61. A portion of the liquid from accumulator 61 can be passed through conduit 62 into an upper portion of fractionator 56 as reflux, while the remainder of the liquid from accumulator 61 is passed through conduit 63, pump 64 and conduits 37 and 33 into reactor 34.

The particular advantage to the present invention is the fact that the heat required by the fractionator 23 can be substantially reduced while still maintaining a very low concentration of the first diluent in the effluent flowing through conduit means 32 to the second stage of the two-stage process. To obtain the first diluent concentration possible by using the stripping column 82 using only the fractionator 23 would require a large amount of energy which is not economical in a commercial process. The present invention is extremely convenient in view of the fact that the hydrogen which is utilized to strip the first diluent in the stripping column 82 is utilized in reactor 13. If the hydrogen were not used in the stripping column 82, the hydrogen would have to be supplied from some other source to the reactor 13. Thus, the hydrogen which must be present in the reactor 13 can be utilized to strip the first diluent from the dinitriles which results in a considerable energy savings for the two-stage process and results in a lower concentration of the first diluent from the first stage of the two-stage process in the second stage of the two-stage process than would be feasible using only the fractionator 23.

The branched-chain unsaturated aliphatic dinitriles which are considered to be advantageously and efficiently hydrogenated in accordance with the process of this invention are the unsaturated dinitriles of the formula

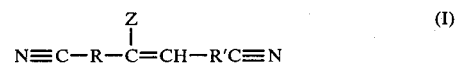

wherein R and R' are independently selected from the group consisting of an alkylene radical and an alkylidene radical, and Z is an alkyl radical. Each R will generally have from 1 to 15 carbon atoms, preferably from 1 to 6, and more preferably from 1 to 3 carbon atoms. Z will generally have from 1 to 15 carbon atoms, preferably from 1 to 6 carbon atoms, and more preferably from 1 to 8 carbon atoms. In general, the unsaturated dinitrile reactant of formula (I) will contain from 7 to 30 carbon atoms, preferably from 8 to 16 carbon atoms, and more preferably from 9 to 12 carbon atoms.

Representative of unsaturated reactant species of formula (I) include such compounds as 3-methyl-3-hexenedinitrile, 3-ethyl-3-hexenedinitrile, 5-methyl-4-nonenedinitrile, 5-methyl-4-decenedinitrile, 7-methyl-6-tridecenedinitrile, 7-methyl-6-pentadecenedinitrile, 12-methyl-12-tetracosenedinitrile, 10-hexyl-9-tetracosenedinitrile, 2,3-dimethyl-3-hexenedinitrile, 2,4,6-trimethyl-3-heptenedinitrile, 4-ethyl-6,7-dimethyl-3-octenedinitrile, 2,4,6-triethyl-3-octenedinitrile, 2-ethyl- 4,6-dipropyl-3-octenedinitrile, 2-methyl-4,6,8,10-tetrapropyl-8-dodecenedinitrile, 2,4,7,9,11,13,15-heptaethyl-6-hexadecenedinitrile, and mixtures of any two or more thereof.

If desired, other olefinically unsaturated reactants can be present and effectively hydrogenated during the hydrogenation of the unsaturated dinitriles of formula (I). Thus, in addition to the unsaturated dinitrile reactants of formula (I), the dinitrile feedstock can contain one or more unsaturated dinitrile reactants of the formula

(II)

wherein each A is independently selected from the group consisting of an alkylene radical and an alkylidene radical. In general, each A will have from 1 to 15 carbon atoms, preferably from 1 to 7 carbon atoms, and more preferably from 1 to 4 carbon atoms. The dinitriles of formula (II) will generally contain from 6 to 30 carbon atoms, preferably from 8 to 16 carbon atoms, and more preferably from 9 to 12 carbon atoms. Representative unsaturated dinitrile reactants of formula (II) include such compounds as 3-methylenehexanedinitrile, 4-methyleneheptanedinitrile, 5-methylenenonanedinitrile, 6-methyleneundecanedinitrile, 7-methylenetridecanedinitrile, 8-methylenepentadecanedinitrile, 12-methylenetrtracosanedinitrile, 15-methylenenonacosanedinitrile, 2-methyl-3-methylenepentadinitrile, 2,4-dimethyl-3-methylenepentanedinitrile, 2-methyl-4-methyleneoctanedinitrile, 2-methyl-7-ethyl-4-methyleneoctanedinitrile, 2,4,8-trimethyl-6-methylenedodecanedinitrile, 2,4,8,10-tetrapropyl-6-methylenedodecanedinitrile, 2,26-dimethyl-14-methyleneheptacosanedinitrile, and mixtures of any two or more thereof.

Unsaturated dinitriles having a structure other than that of formulas (I) and (II) can be present during the hydrogenation reaction, if desired. Similarly, other compounds which may be found in the feed souce of the dinitriles of Formulas (I) and (II) can be present so long as such additional compounds do not significantly adversely affect the hydrogenation of the dinitriles of formulas (I) and (II). Where other dinitriles are present in the feedstock, the dinitriles of formula (I) will generally constitute at least 0.1 weight percent of the total dinitriles. The significant advantages of the process increase with increasing concentrations of the dinitriles of formula (I) in the feedstock. Thus, the process is even more advantageous for concentrations of the dinitriles of formula (I) in the feedstock of at least 5 weight percent. The process is considered to be particularly advantageous for dinitrile feedstocks having a concentration of the dinitriles of formula (I) of at least 10 weight percent.

A presently preferred branched-chain olefinically unsaturated aliphatic dinitrile feedstock for employment in the practice of this process is the dinitrile reaction product mixture obtained by the reaction of isobutylene and acrylonitrile. This dinitrile reaction product mixture generally comprises 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile. The first four named compounds in this mixture are of the type of formula (I), while the last three named compounds in this mixture are of the type of formula (II). The weight ratio of the dinitriles of formula (I) to the dinitriles of formula (II) in this mixture is generally in the range of about 10:1 to 1:10.

Reactor 13 contains a suitable catalyst for the hydrogenation of the olefinic unsaturation, generally without significant reduction of the nitrile radical. Suitable catalysts for employment in the present invention include elemental palladium and compounds of palladium which are reducible by hydrogen under the reaction conditions in reactor 13 to the finely divided elemental metal. Suitable reducible compounds include palladium oxide, palladium chloride, palladium nitrate, palladium oxalate, palladium acetate, palladium carbamate, palladium propionate, palladium tartrate, palladium hydroxide, and the like, and mixtures of any two or more thereof.

Reactor 34 contains a suitable catalyst for the hydrogenation of the nitrile groups and any remaining olefinic unsaturation. Suitable catalysts for employment in the present invention include elemental ruthenium and compounds of ruthenium which are reducible by hydrogen under the reaction conditions in reactor 34 to the finely divided elemental metal, and mixtures of any two or more thereof. Specific examples of suitable catalysts include elemental ruthenium, ruthenium oxide, ruthenium nitrate, ruthenium carbamate, ruthenium hydroxide, ruthenium oxalate, ruthenium acetate, ruthenium chloride, ruthenium tartrate, ruthenium propionate, and the like, and mixtures of any two or more thereof.

In the practice of this process it is often desirable to employ catalytic amounts of the elemental metal, reducible compounds of the metal catalysts or mixtures thereof supported by a solid catalyst carrier which does not deleteriously affect the catalytic hydrogenation process. Such supports include, for example, carbon, kieselguhr, silica, alumina, silica-alumina, calcium carbonate, barium carbonate, asbestos, pumice, clays, and the like, and mixtures of any two or more thereof. The elemental metal or reducible compound catalyst components can be added to the catalyst support by any of the methods well known in the art. For example, the supported catalysts can be prepared by dry mixing the components or by impregnating the support with a solution or dispersion of the metal catalyst in elemental form or in the form of reducible compounds thereof. The supported catalyst can be pretreated with hydrogen to reduce the compounds, or such reduction can be achieved in the hydrogenation reactor. When a support is employed, the total elemental metal catalyst will generally be in the range of about 0.5 to about 50 weight percent, preferably in the range of about 1 to about 10 weight percent, based on the weight of the total catalyst composition. A presently preferred catalyst for first stage reactor 13 is palladium on carbon with the palladium content being about 5 weight percent of the total catalyst for reactor 13. A presently preferred catalyst for second stage reactor 34 is ruthenium on alumina, the ruthenium metal content being about 5 percent by weight, based on the weight of the total catalyst for reactor 34. These presently preferred catalysts, as well as other suitable catalyst such as 5 weight percent ruthenium on charcoal, are available commercially.

Any catalytic hydrogenation temperature can be employed which provides the desired degree of catalytic efficiency in the hydrogenation of the branched-chain unsaturated aliphatic dinitrile containing feedstock. It is desirable that the temperature in the first stage reaction be at least 100° C., preferably at least 120° C., and more preferably at least about 130° C. in order to provide at least substantially complete reduction of olefinic unsaturation with a reasonable catalyst life. On the other hand, it is desirable that the first stage reaction temperature be less than 175° C., preferably less than 160° C., and more preferably less than 150° C. in order to provide a greater catalyst life and to reduce the production of heavies. Thus, the hydrogenation temperatures in the first stage will generally be within the range of about 100° C. to about 175° C., preferably will be within the range of about 120° C. to about 160° C., and more preferably will be within the range of about 130° C. to about 150° C. The hydrogenation temperatures in the second stage will generally be within the range of about 80° C. to about 250° C., and preferably will be within the range of about 199° C. to about 200° C.

The catalytic hydrogenation of the difficultly reducible carbon to carbon double bond illustrated in formula (I) can be carried out in the first stage at any suitable hydrogenation pressure. The catalytic hydrogenation of branched-chain saturated aliphatic dinitriles can be carried out in the second stage at any hydrogen pressure wherein the nitrile groups are reduced in the presence of the secondary amine formation suppressant, hydrogen and a suitable diluent. Generally, suitable hydrogen pressures for both stages are within the range of from about 500 to about 5000 psig (3.45 to 34.5 MPa), but lower or even higher hydrogen pressures can be employed. Preferably, due to economic consideration, hydrogen pressures within the range of about 1000 to about 3000 psig (6.9 to 20.7 MPa) are employed. It may be desirable to employ higher hydrogen pressures at lower reaction temperatures to achieve the desired degree of hydrogenation within a reasonable amount of time.

Any time interval suited for the desired catalytic hydrogenation in each stage can be employed in the practice of this process. However, time intervals economically attractive to the process are generally within the range of about 15 minutes to about 5 hours for the first stage of a batch hydrogenation process, and generally within the range of about 15 minutes to about 5 hours for the second stage of the batch process. A total reaction time in the range of about 1 to about 6 hours is presently preferred in order to insure substantially complete hydrogenation of any unsaturated olefinic bonds in the feedstock as well as complete hydrogenation of the nitrile groups to primary amino groups. The catalytic hydrogenation of unsaturated dinitriles in accordance with the process can be carried out as a continuous process at any suitable liquid hourly space velocity (LHSV). However, the total liquid hourly space velocity rates for both reactors will generally be within the range of about 0.1 to about 10, more preferably from about 0.5 to about 5 volumes of dinitrile reactant plus diluent per volume of catalyst (including the volume of any catalyst support if any is present) per hour.

The stripper 82 may be operated under any suitable process conditions. In general, the temperature in the upper portion of the stripper 82 will be about 300° F. (149° C.). The temperature in the lower portion of the stripper 82 will be about 295° F. (146° C.). The pressure in the upper portion of the stripper 12 will be about 18 psia (124 kPa). The hydrogen will typically be maintained at about 100° F. (38° C.) and a flow rate of 174 lbs/hr. The accumulator 87 temperature will be about 100° F. (38° C.) while the reflux rate will be about 74.9 lb/hr. The stripper 82 will preferably have from about 2 to about 6 equilibrium stages.

The diluent for the first stage reaction, i.e. the reduction of the olefinic unsaturation, is composed, at least predominately, of at least one alkanol having 1 to 3 carbon atoms. While the first stage diluent can contain a minor amount of water or another suitable codiluent, it preferably consists generally of at least one of methanol, ethanol, isopropanol and n-propanol, and more preferably consists of methanol.

The diluent for the second stage reaction, i.e. the reaction of the nitrile groups, can be any suitable diluent, but is preferably at least predominately composed of at least one member selected from the group consisting of the unsubstituted tertiary alkanols having from 4 to 12 carbon atoms per molecule, saturated hydrocarbons having from 4 to 12 carbon atoms per molecule, unsubstituted acyclic and unsubstituted cyclic ethers having 4 to 12 carbon atoms per molecule, and mixtures of any two or more thereof. The term "unsubstituted" indicates that there are no substituents other than hydrocarbyl radicals. Examples of tertiary alkanol diluents include 2-methyl-2-propanol, 2-methyl-2-butanol, 2-ethyl-2-hexanol, 2,4-dimethyl-2-pentanol, 2,3-dimethyl-3-pentanol, 3-ethyl-3-pentanol, 3,7-dimethyl-3-octanol, 3-ethyl-3-decanol, and the like, and mixtures of any two or more thereof. Examples of saturated hydrocarbons, i.e. alkanes and cycloalkanes, include butane, pentane, hexane, decane, dodecane, cyclobutane, cyclopentane, cyclohexane, cyclodecane, cyclododecane, 2-methylbutane, methylcyclopentane, 2,2,4-trimethylpentane, and mixtures of any two or more thereof. Examples of ethers include 1,3-dioxane, 1,4-dioxane, tetrahydrofuran, 4,4-dimethyl-1,3-dioxane, and mixtures of any two or more thereof. The primary and secondary alkanols are not considered to be suitable for employment in the second stage reaction of this process because of the resulting N-alkylation reaction, which would substantially reduce the production of the desired primary diamines. Thus when the diluent for the second stage reaction comprises any additional component other than an unsubstituted tertiary alkanol, a saturated hydrocarbon or an unsubstituted ether, the additional component should be one which does not have any significant adverse effect on the desired hydrogenation reaction.

To facilitate handling of the reaction mixtures, the weight ratio of unsaturated dinitrile reactants to diluent charged to the first reaction zone 13 will generally be within the range of about 0.001:100 to about 50:100, and is preferably in the range of about 0.1:100 to about 20:100. Similarly the weight of ratio of saturated dinitrile reactants to diluent charged to the second reaction zone 34 will generally be within the range of about 0.001:100 to about 50:100, and is preferably in the range of about 0.1:100 to about 20:100.

A secondary amine formation suppressant, e.g. ammonia, is employed in the second stage of the process as a means for suppressing undesirable side reactions such as the formation of secondary and tertiary amines. Any amount of the secondary amine formation suppressant can be employed which is effective in deterring or reducing undesirable side reactions. In general, the mole ratio of the secondary amine formation suppressant to cyano group (there being two cyano groups in each saturated dinitrile) will be in the range of about 1:1 to about 25:1, and preferably will be in the range of about 7:1 to about 15:1.

The following calculated example is presented in further illustration of the invention and should not be construed in undue limitation thereof. In the calculated example the olefinically unsaturated dinitriles which are being hydrogenated are a mixture obtained by the reaction of isobutylene and acrylonitrile. This unsaturated dinitrile mixture comprises 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile. For convenience, this mixture will be described in the calculated example as diadduct. This diadduct can be hydrogenated to produce a valuable saturated diamine for use in the preparation of polyamides and other polymers. In such applications, it has been found to be highly desirable that essentially none of the olefinic unsaturation remains in the final hydrogenation product and that the final hydrogenation product be at least substantially free of cyano groups. Thus, it is important that the carbon-carbon olefinic double bonds and the nitrile groups in the diadduct be reduced efficiently in the hydrogenation process employed.

It is further important that the diluent utilized in the first stage of the two-step process be substantially removed from the reaction effluent of the first stage of the two-stage process before the reaction effluent is introduced into the second stage of the two-stage process to reduce N-alkylation.

EXAMPLE

Table I illustrates a calculated material balance for 80 million pound per year plant in pounds per hour for the stripper 82. The flow rate of each component has been calculated and is listed in Table I.

TABLE I

| | Material Balance for 80mm LB/Yr Plant In Lb/Hr for the Stripper 82 | | | | | |
|---|---|---|---|---|---|---|
| Component | Flow In Conduit 81 | Flow In Conduit 83 | Flow In Conduit 84 | Flow In Conduit 90 | Flow In Conduit 91 | Flow In Conduit 32 |
| Hydrogen | | 174 | 174 | | 174 | |
| Diluent | 10 | | 11.93 | 2.1 | 9.83 | 0.17 |
| Acrylonitrile Dimers | 168 | | 16.2 | 16.2 | | 168 |
| Diadduct | 10,760 | | 50.9 | 50.9 | | 10,760 |
| Heavies | 803 | | 5.7 | 5.7 | | 803 |

As is illustrated in Table I, the flow rate of the diluent in the effluent flowing through the conduit means 81 is calculated to be 10 pounds per hour. In contrast, the flow rate of the diluent in the effluent flowing through conduit means 32 is calculated to be 0.17 pounds per hour. This illustrates the significant improvement provided by the stripping column 82. This improvement could not be gained using the fractionator 23 without the expenditure of considerable energy which would not be economically feasible in a commercial process.

Reasonable variations and modifications are possible within the scope of the foregoing disclosure and the appended claims to the invention.

That which is claimed is:

1. Apparatus comprising:
   a first reactor means;
   means for introducing an olefinically unsaturated dinitrile feedstock into said first reactor means, said introducing means including a source means for said feedstock;
   means for introducing a first diluent into said first reactor means, said introducing means including a source means for said diluent;
   means for introducing hydrogen into said first reactor means, said introducing means including a source means for said hydrogen;
   a fractionation column means;
   means for withdrawing the reaction effluent from a lower portion of said first reactor means and for introducing said reaction effluent into said fractionation column means;
   means for withdrawing at least a portion of said first diluent as an overhead product from said fractionation column means;
   a stripping column means;
   means for withdrawing a first intermediate dinitrile product containing a reduced concentration of said first diluent as a bottom product from said first fractionation column means and for supplying said first intermediate dinitrile product to said stripping column means;
   means for supplying hydrogen to said stripping column means, said supplying means including a source means for said hydrogen;
   means for withdrawing the hydrogen supplied to said stripping column means and at least a portion of said first diluent remaining in said first intermediate dinitrile product from said stripping column means as an overhead product from said stripping column means;
   a second reactor means; and
   means for removing a second intermediate dinitrile product having a substantially reduced concentration, if any, of said first diluent as a bottoms product from said stripping column means and for supplying said second intermediate dinitrile product to said second reactor means.

2. Apparatus in accordance with claim 1 wherein said first reactor means contains a first catalyst, said first catalyst comprising at least one catalytic component selected from the group consisting of elemental palladium and compounds of palladium which are reducible by hydrogen to elemental palladium.

3. Apparatus in accordance with claim 2 wherein said first diluent comprises at least one member selected from the group consisting of alkanols having 1 to 3 carbon atoms and including a source means for said alkanols.

4. Apparatus in accordance with claim 1 wherein said means for withdrawing the reaction effluent from a lower portion of said first reactor and for introducing said reaction effluent into said fractionation column means comprises:
   a flash tank means;

means for withdrawing the reaction effluent from a lower portion of said first reactor means and for introducing said reaction effluent into said flash tank means;

means for withdrawing hydrogen as an overhead product from said flash tank means; and means for withdrawing the reaction effluent from which the hydrogen has been removed as a bottoms product from said flash tank means and for introducing the reaction effluent from which the hydrogen has been removed into said fractionation column means.

5. Apparatus in accordance with claim 4 additionally comprising:

means for recycling the overhead product from said flash tank means to said first reactor means;

means for recycling the overhead product from said fractionation column means to said first reactor means; and means for recycling the overhead product from said stripping column means to said first reactor means.

6. Apparatus in accordance with claim 5 wherein said second reactor means contains a second catalyst, said second catalyst comprising at least one catalytic component selected from the group consisting of elemental ruthenium and compounds of ruthenium which are reducible by hydrogen to elemental ruthenium.

7. Apparatus in accordance with claim 6 additionally comprising:

means for supplying hydrogen to said second reactor means;

means for supplying a second diluent to said second reactor means, said second diluent being at least substantially free of any component having an adverse affect on the hydrogenation of said nitrile group and being at least predominantly composed of at least one member selected from the group consisting of unsubstituted tertiary alkanols having 4 to 12 carbon atoms per molecule, saturated hydrocarbons having 4 to 12 carbon atoms per molecule and unsubstituted ethers having 4 to 12 carbon atoms per molecule;

means for supplying a suitable secondary amine formation suppressant to said second reactor means; and means for withdrawing the reaction product from a lower portion of said second reactor means.

* * * * *